(12) United States Patent
Chen

(10) Patent No.: US 12,063,962 B2
(45) Date of Patent: *Aug. 20, 2024

(54) ATOMIZER, ATOMIZING ASSEMBLY AND INHALER

(71) Applicant: SHENZHEN SMOORE TECHNOLOGY LIMITED, Shenzhen (CN)

(72) Inventor: Zhiping Chen, Shenzhen (CN)

(73) Assignee: SHENZHEN SMOORE TECHNOLOGY LIMITED, Shenzhen (CN)

(*) Notice: Subject to any disclaimer, the term of this patent is extended or adjusted under 35 U.S.C. 154(b) by 736 days.

This patent is subject to a terminal disclaimer.

(21) Appl. No.: 16/942,301

(22) Filed: Jul. 29, 2020

(65) Prior Publication Data

US 2021/0001057 A1    Jan. 7, 2021

Related U.S. Application Data

(63) Continuation of application No. 15/926,683, filed on Mar. 20, 2018, now Pat. No. 10,786,634, which is a
(Continued)

(51) Int. Cl.
*A24F 40/40* (2020.01)
*A24F 40/10* (2020.01)
(Continued)

(52) U.S. Cl.
CPC .............. *A24F 40/40* (2020.01); *A24F 40/44* (2020.01); *A61M 11/04* (2013.01);
(Continued)

(58) Field of Classification Search
CPC .......... A24F 40/10; A24F 40/40; A24F 40/42; A24F 40/44; A24F 40/46; A61M 11/041; A61M 11/042
See application file for complete search history.

(56) References Cited

U.S. PATENT DOCUMENTS 8,499,766 B1   8/2013 Newton
9,956,357 B2 * 5/2018 Chen .................. A61M 11/04
(Continued)

FOREIGN PATENT DOCUMENTS

CA        2641869        5/2010
CN     101843368 A       4/2010
(Continued)

OTHER PUBLICATIONS

European Search Report EP15159785.
(Continued)

*Primary Examiner* — Joseph D. Boecker
(74) *Attorney, Agent, or Firm* — Weiss & Moy, PC; Jeffrey D. Moy

(57) ABSTRACT

An atomizer for an inhaler includes a housing, a gasket, a liquid absorbing sheet, a wick, and an atomizing element. The housing includes a first housing and a second housing, the first housing and the second housing form a liquid reservoir therebetween for storing liquid. The gasket is sleeved on the first housing, the gasket defines a liquid conducting hole in communication with the liquid reservoir. The liquid absorbing sheet is sleeved on the first housing in contact with the gasket, the liquid absorbing, sheet is configured to absorb the liquid in the liquid reservoir via the liquid conducting hole. The wick is in contact with the liquid absorbing sheet and configured to draw the liquid from the liquid absorbing sheet. The atomizing element is fixed to the wick and configured to atomize the liquid in the wick.

11 Claims, 11 Drawing Sheets

Related U.S. Application Data continuation of application No. 14/666,053, filed on Mar. 23, 2015, now Pat. No. 9,956,357.

(51) Int. Cl.
- *A24F 40/44* (2020.01)
- *A61M 11/04* (2006.01)
- *A61M 15/00* (2006.01)
- *A61M 15/06* (2006.01)
- *A61M 16/14* (2006.01)

(52) U.S. Cl.
CPC ...... *A61M 11/042* (2014.02); *A61M 15/0021* (2014.02); *A61M 15/06* (2013.01); *A61M 16/142* (2014.02); *A24F 40/10* (2020.01); *A61M 2205/82* (2013.01); *A61M 2205/8206* (2013.01)

(56) References Cited

U.S. PATENT DOCUMENTS

| | | | |
|---|---|---|---|
| 10,786,634 B2 * | 9/2020 | Chen | A61M 15/0021 |
| 2008/0257367 A1 | 10/2008 | Paterno | |
| 2013/0192615 A1 | 8/2013 | Tucker | |
| 2013/0192617 A1 | 8/2013 | Thompson | |
| 2013/0319438 A1 * | 12/2013 | Liu | A24F 40/485 131/329 |
| 2014/0007863 A1 * | 1/2014 | Chen | A24F 40/485 128/200.14 |
| 2014/0150783 A1 * | 6/2014 | Liu | A24F 40/40 128/202.21 |
| 2014/0150785 A1 * | 6/2014 | Malik | A61M 11/042 128/202.21 |
| 2014/0202475 A1 | 7/2014 | Liu | |
| 2014/0209105 A1 | 7/2014 | Sears | |
| 2014/0216450 A1 | 8/2014 | Liu | |
| 2014/0261486 A1 | 9/2014 | Potter | |
| 2014/0261496 A1 * | 9/2014 | Liu | A24F 40/485 131/329 |
| 2014/0283823 A1 | 9/2014 | Liu | |
| 2014/0290676 A1 * | 10/2014 | Liu | A24F 40/485 131/329 |
| 2014/0299139 A1 * | 10/2014 | Liu | A24F 40/485 131/329 |
| 2015/0128970 A1 | 5/2015 | Liu | |
| 2016/0286864 A1 * | 10/2016 | Lin | A24F 40/485 |

FOREIGN PATENT DOCUMENTS

| | | |
|---|---|---|
| CN | 101528549 | 3/2011 |
| CN | 102326869 | 1/2012 |
| CN | 202618275 U | 4/2012 |
| CN | 202611875 | 12/2012 |
| CN | 202618275 | 12/2012 |
| CN | 102970885 | 3/2013 |
| CN | 103237470 | 8/2013 |
| CN | 203353683 | 12/2013 |
| CN | 203538385 | 4/2014 |
| CN | 203538385 U * | 4/2014 |
| CN | 103879939 | 6/2014 |
| CN | 203692550 | 7/2014 |
| CN | 103960781 | 8/2014 |
| CN | 104026745 A | 9/2014 |
| CN | 104039182 | 9/2014 |
| CN | 104055223 | 9/2014 |
| CN | 104055223 A | 9/2014 |
| CN | 20424515 U | 10/2014 |
| CN | 104366095 | 2/2015 |
| CN | 104366695 A | 2/2015 |
| CN | 204245152 | 4/2015 |
| FR | 3003442 | 9/2014 |
| WO | 2013147492 | 10/2013 |
| WO | 2014146232 | 9/2014 |

OTHER PUBLICATIONS

European Search Report EP15854111.
European Search Report EP18164558.
European Search Report EP18164559.
International Search Report PCT/CN2015/083652.
1st Office Action: 201410597265.4 Shenzhen Michael Technology Co. Ltd.
2nd Office Action: 201410597265.4 Shenzhen Michael Technology Co. Ltd.
European Search Report EP15159785 Applicant: Shenzhen Smoore Technology Limited dated Mar. 18, 2016.
European Search Report EP15854111 Applicant: Shenzhen Smoore Technology Limited dated Jul. 11, 2018.
European Search Report EP18164558 Applicant: Shenzhen Smoore Technology Limited dated Aug. 6, 2018.
European Search Report EP18164559 Applicant: Shenzhen Smoore Technology Limited dated Aug. 14, 2018.
International Search Report PCT/CN2015/083652 Applicant: Shenzhen Smoore Technology Limited dated Mar. 9, 2015.
1st Office Action: 201410597265.4 Shenzhen Michael Technology Co. Ltd. dated Jul. 5, 2017.
2nd Office Action: 201410597265.4 Shenzhen Michael Technology Co. Ltd dated Nov. 30, 2016.
3rd Office Action: 201410597265.4 Shenzhen Michael Technology Co. Ltd dated Apr. 1, 2017.
1st Office Action of CN201410597265.4 Shenzhen Michael Technology Co. Ltd. dated Jul. 5, 2016.
International Search Report PCT/CN2015/083652 Applicant: Shenzhen Smoore Technology Limited dated Sep. 2, 2015.
First Chinese Office Action, dated Jun. 1, 2016.
Second Chinese Office Action, dated Jan. 25, 2017.

* cited by examiner

ATOMIZER, ATOMIZING ASSEMBLY AND INHALER

CROSS REFERENCE TO RELATED APPLICATIONS

The present application is a continuation application of U.S. application Ser. No. 15/926,683, filed Mar. 20, 2018, now allowed, which is a continuation application of U.S. application Ser. No. 14/666,053, filed Mar. 23, 2015, now allowed, which claims priority to Chinese application No. 201410597265.4, flied Oct. 29, 2014. The disclosures of the above identified applications are hereby incorporated herein in their entireties by reference.

FIELD OF THE INVENTION

The present disclosure relates to devices used for delivering atomizing medium into the body, and more particularly relates to an atomizer, an atomizing assembly, and an inhaler having the same.

BACKGROUND OF THE INVENTION

Inhaler is a device used for delivering atomized liquid into the body via the lungs, which is usually represented by a medical inhaler used in the treatment of asthma and an electronic cigarette for replacing cigarettes.

Similar to the medical inhaler, the conventional electronic cigarette usually employs an atomizing element to atomize the liquid in a wick. However, it is often difficult to control the amount of the liquid in the wick. One effective approach to improve the control accuracy of the amount of liquid is to employ two elements with different liquid conducting rates, such that the liquid can pass these elements orderly, thereby increasing the control accuracy of the amount of liquid. However, this approach exists some disadvantages, such as difficulty to assemble and higher cost.

SUMMARY OF THE INVENTION

The present disclosure is directed to an atomizer which can accurately control of the amount of liquid and is easy to be assembled and has a low cost.

An atomizer for an inhaler includes a housing, a gasket, a liquid absorbing sheet, a wick, and an atomizing element. The housing includes a first housing and a second housing, the first housing is at least partially positioned in the second housing, the first housing defining an air flow passage therein; the first housing and the second housing form a liquid reservoir therebetween for storing liquid. The gasket is sleeved on the first housing, the gasket defines a liquid conducting hole in communication with the liquid reservoir. The liquid absorbing sheet is sleeved on the first housing in contact with the gasket, the liquid absorbing sheet is configured to absorb the liquid in the liquid reservoir via the liquid conducting hole. The wick is in contact with the liquid absorbing sheet and configured to draw the liquid from the liquid absorbing sheet. The atomizing element is fixed to the wick and configured to atomize the liquid in the wick.

The number of the liquid conducting hole is plural, and at least one liquid conducting hole has a non-circular shape.

The housing further comprises a third housing formed by an edge of the second housing extending in a direction away from the second housing; the third housing defines a cavity therein, and the gasket and the liquid absorbing sheet are received in the cavity; the liquid absorbing sheet is in contact with an inner wall of the third housing on an edge thereof.

The atomizer further includes an atomizing base defining an atomizing cavity, wherein the atomizing base defines an opening at an end thereof and defines a through hole in communication with the atomizing cavity and an outside at the other end thereof; the wick is located in the atomizing cavity; an edge of the atomizing base having the opening is in contact with the liquid absorbing sheet.

The atomizing base is made of elastic material and defines a wire through hole thereon; the atomizing element comprises a wire extending through the wire through hole.

The wick comprises a plurality of fiber filaments; the plurality of fiber filaments located at the end of the wick are separated; at least part of the ends of the plurality of fiber filaments are in contact with the liquid absorbing sheet, the other ends of the plurality of fiber filaments are clamped between the atomizing base and the liquid absorbing sheet.

At the end of the wick where the plurality of fiber filaments are separated, a length of the fiber filament with ends being in contact with the liquid absorbing sheet is less than a length of the fiber filament with ends being clamped between the atomizing base and the liquid absorbing sheet.

The wick has two ends, each end of the wick is located on opposite sides of the first housing; the atomizing element comprises a heating wire coiled around a middle portion of the wick; the first housing defines an opening in communication with the air flow passage and the atomizing cavity; the through hole is in correspondence with the opening; the heating wire is positioned between the through hole and the opening, and a distance between the heating wire and the first housing is greater than 2 mm.

The atomizer further includes a negative electrode connecting element, wherein the negative electrode connecting element comprises a negative electrode connecting element body and a boss located at an outer periphery of the negative electrode connecting element body; the negative electrode connecting element body and the boss are conductors; the negative electrode connecting element body is electrically connected to the boss; the atomizing base is received in the cavity of the third housing; part of the negative electrode connecting element body extends through the cavity and is in contact with the atomizing base; the negative electrode connecting element body is electrically connected to a negative electrode of the atomizing element; the negative electrode connecting element body defines an air inlet in communication with the air flow passage and an outside of the negative electrode connecting element body.

An atomizing assembly for an inhaler includes a sleeve, a mouthpiece located at an end of the sleeve; and the forgoing atomizer received in the sleeve.

An inhaler includes a power assembly, the forgoing atomizing assembly fixed to the power assembly and electrically connected to the power assembly.

These and other objects, advantages, purposes and features will become apparent upon review of the following specification in conjunction with the drawings.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION OF THE EMBODIMENTS

Reference will now be made to the drawings to describe, in detail, embodiments of the present atomizer, atomizing assembly, and inhaler. It should be noted that references to "an" or "one" embodiment in this disclosure are not necessarily to the same embodiment, and such references mean at least one.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein,""above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

An atomizer according to an embodiment can be a component of an inhaler used to atomize (vaporize) the liquid into vapor, which then can be delivered into human body. The inhaler can be an electronic cigarette, or a medical metered-dose inhaler, or the like.

Figure 1:
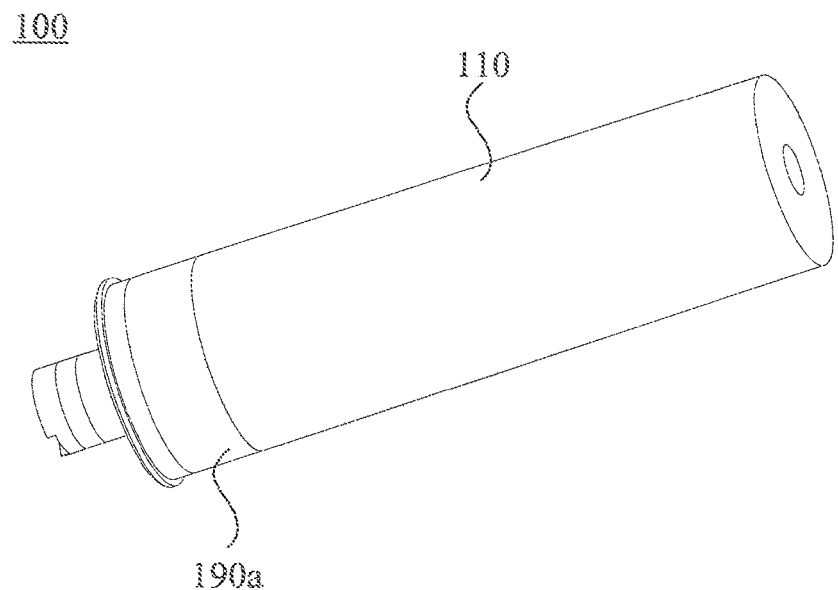
FIG. 1 is a perspective view of an embodiment of an atomizer for an inhaler.
Figure 2:
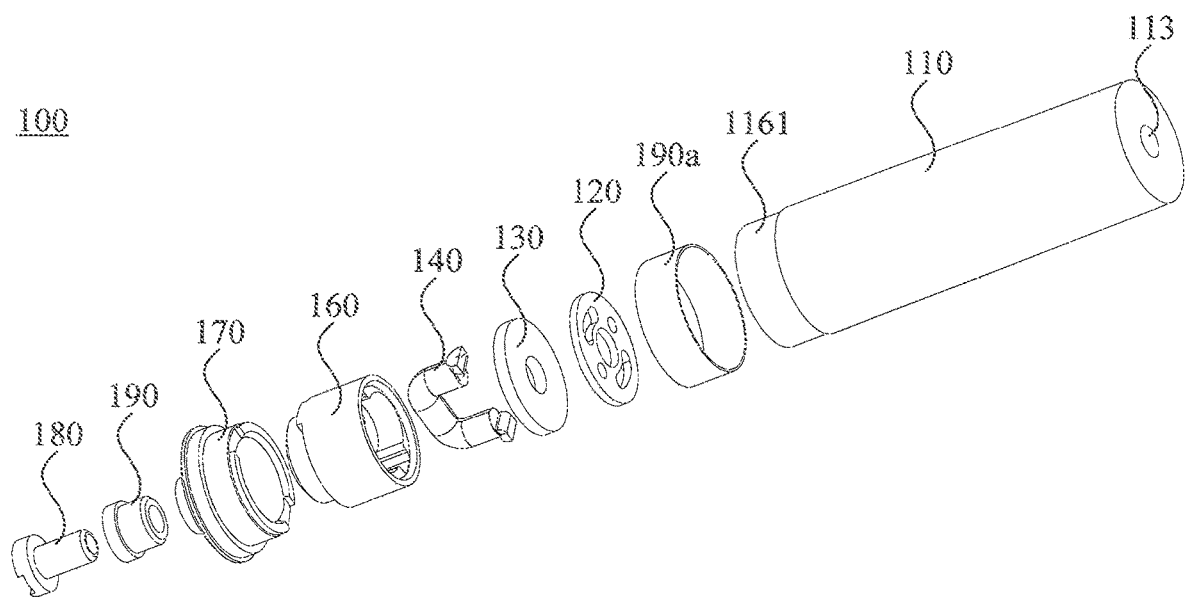
FIG. 2 is an exploded perspective view of the atomizer for the inhaler of FIG. 1.
Figure 3:
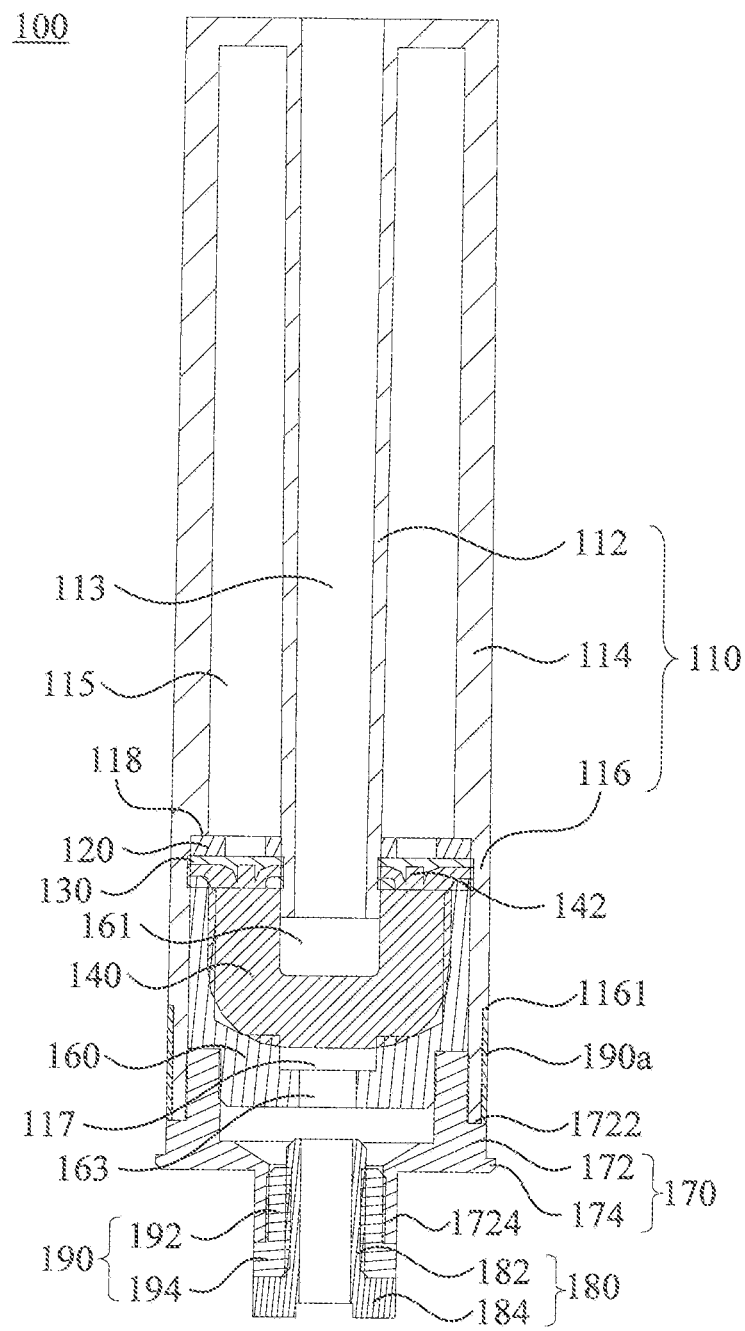
FIG. 3 is an cross-sectional view of the atomizer for the inhaler of FIG. 1.

Referring to FIG. 1 to FIG. 3, an embodiment of the atomizer 100 includes a housing 110, a gasket 120, a liquid absorbing sheet 130, a wick 140, and an atomizing element (not shown). The housing 110 includes a first housing 112 and a second housing 114. The first housing 112 is at least partially positioned in the second housing 114. The first housing 112 and the second housing 114 are preferably integrally formed. The first housing 112 defines an air flow passage 113 therein. A liquid reservoir 115 for storing liquid is formed between the first housing 112 and the second housing 114. In the case that the inhaler is an electronic cigarette, the liquid stored in the liquid reservoir 115 can be a liquid solution known as e-liquid; while the liquid can also be medication solution in the case that the inhaler is a medical inhaler.

The gasket 120 and the liquid absorbing sheet 130 are both sleeved on the first housing 112, and the gasket 120 is located between the liquid reservoir 115 and the liquid absorbing sheet 130. The gasket 120 defines a liquid conducting hole 122 in communication with the liquid reservoir 115. A side of the liquid absorbing sheet 130 is in contact with the gasket 120, such that the liquid absorbing sheet 130 can absorb the liquid in the liquid reservoir 115 and store, it temporarily. The other side of the liquid absorbing sheet 130 is in contact with the wick 140, which is used to absorb the liquid from the liquid absorbing sheet 130. The atomizing element is fixed to the wick 140 and is used to atomize the liquid in the wick 140.

The liquid stored in the liquid reservoir 115 can reach the liquid absorbing sheet 130 via the liquid conducting hole 122 on the gasket 120, such that it can be absorbed by the liquid absorbing sheet 130. The liquid of the liquid absorbing sheet 130 will then be absorbed by the wick 140, and finally atomized by the atomizing element. The gasket 120 has a very large liquid-passing rate, and the amount of liquid passing through the gasket 120 can be roughly controlled by the number and the diameter of the liquid conducting hole 122. The liquid absorbing sheet 130 has a low liquid-passing rate, and the amount of liquid passing through the liquid absorbing sheet 130 can be precisely controlled. Due to the cooperation of the gasket 120 and the liquid absorbing sheet 130, the control accuracy of the amount of the liquid of the wick 140 can be effectively increased.

Figure 4:
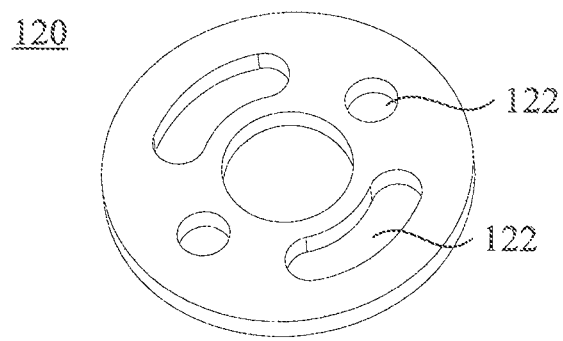
FIG. 4 is a perspective view of a gasket of the atomizer for the inhaler of FIG. 1.

Since the gasket 120 and the liquid absorbing sheet 130 are both sleeved on the first housing 112, they can be simply assembled by using the first housing 112 as a reference. To facilitate the assembly, the gasket 120 is preferably made of rigid material. The gasket 120 has a sheet-like structure. In one embodiment, the gasket 120 can be a plastic sheet with holes, which has a low cost. The number of liquid conducting hole 122 can be single or plural. Referring to FIG. 4, in the illustrated embodiment, there are four liquid conducting holes 122, which are symmetrically distributed on the gasket 120. It should be noted that, circular hole is not favorable, because the liquid in the liquid reservoir 115 has a large viscosity and surface tension, and the liquid tends to form a stable film in the surface of the circular hole, which is difficult for the liquid to leak out. Accordingly, at least one liquid conducting holes 122 has a non-circular shape, which can ensure a smooth pass through of the liquid for it is not easy to produce a film.

In one embodiment, the housing 110 further includes a third housing 116. The third housing 116 is formed by extending an edge of the second housing 114 in a direction away from the second housing 114. The third housing 116 defines a cavity 117 therein. The gasket 120 and the liquid absorbing sheet 130 are received in the cavity 117. It is to be understood that, in alternative embodiments, the gasket 120 can be in contact with the second housing 114 directly, and the second housing 114, the gasket 120, and the liquid absorbing sheet 130 can be fixed together through other structures.

In the illustrated embodiment, the first housing 112, the second housing 114, and the third housing 116 are preferably integrally formed. The first housing 112, the second housing 114, and the third housing 116 can all be tubular. The third housing 116 has a greater inner diameter than that of the second housing 114. A stepped portion 118 is formed between the second housing 114 and the third housing 116. The gasket 120 can be latched in the stepped portion 118, thus the assembly is simple and reliable.

In one embodiment, the liquid absorbing sheet 130 is in contact with the inner wall of the third housing 116 on an edge thereof, such that the liquid reservoir 115 is isolated from the cavity 117. The liquid absorbing sheet 130 can prevent the liquid from flowing from the liquid reservoir 115, thus ensuring a sealing between the liquid reservoir 115 and the air flow passage 113.

Figure 5:
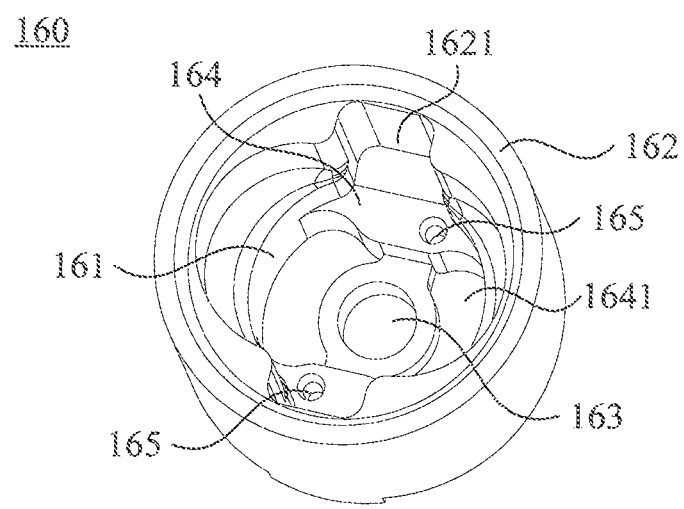
FIG. 5 is a perspective view of an atomizing base of the atomizer for the inhaler of FIG. 1.
Figure 6:
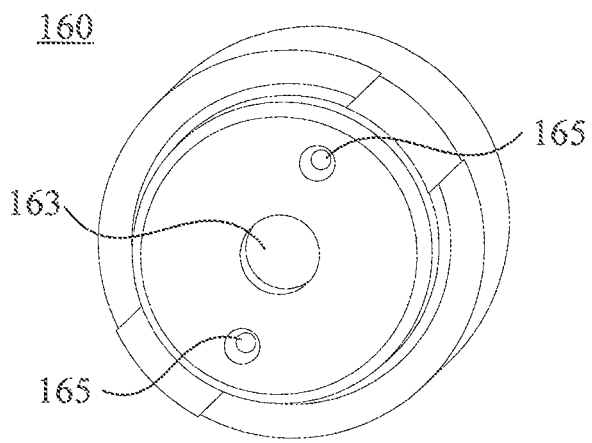
FIG. 6 is similar to FIG. 5, but viewed from another aspect.

Referring to FIG. 5 and FIG. 6, the atomizer 100 further includes an atomizing base 160. The atomizing base 160 defines an atomizing cavity 161 therein. The atomizing base 160 defines an opening at an end thereof and defines a through hole 163 at the other end thereof in communication with the atomizing cavity 161 and an outside of the atomizing base 160. The wick 140 is at least partially located in the atomizing cavity 161. An edge of the atomizing base 160 having the opening is in contact with the liquid absorbing sheet 130. The atomizing base 160 can provide a space for atomizing, and air can enter the atomizing cavity 161 from the through hole 163 and bring the atomized liquid into the air flow passage 113, and inhaled into the mouth of the user.

The atomizing element includes a wire (not shown). The atomizing element is located in the atomizing cavity 161, and the wire extends through the atomizing base 160. In one embodiment, the atomizing base 160 is made of elastic material and defines a wire through hole 165 thereon. Referring to FIG. 5 and FIG. 6, the wire through hole 165 is formed by a blind hole being extended through by the wire. When the wire extends the wire through hole 165, the atomizing base 160 can seal the wire through hole 165 due to its resiliency, such that avoiding the liquid from leaking out of the atomizing cavity 161 along the wire.

In addition, the atomizing base 160 includes a sidewall 162 and a bottom surface 164. The sidewall 162 has a tubular shape with a short length, and the bottom surface 164 is positioned at a side of the sidewall 162. The wire through hole 165 and the through hole 163 are defined at the bottom surface 164. Referring to FIG. 5, in one embodiment, the sidewall 162 defines a groove 1621 to match the wick 140, such that the wick 140 can be accurately located and not prone to move. In one embodiment, the bottom surface 164 defines a groove 1641 to receive the liquid dropping from the wick 140, such that the liquid dropping from the wick 140 is not easy to accumulate around the wire, further avoiding the liquid from leaking out of the, atomizing cavity 161 along the wire.

Referring also to FIG. 3, in one embodiment, the wick 140 includes a plurality of fiber filaments 142. The plurality of fiber filaments 142 located at the end of the wick 140 are separated, which can be obtained by disperse the top end of the wick 140. The separated fiber filaments 142 can increase a contact area thereof with the liquid absorbing sheet 130, thereby increasing the liquid conducting rate between the fiber filaments 142 and the liquid absorbing sheet 130.

The wick 140 has two ends, and each end is located at opposing side of the first housing 112. Additionally, in one embodiment, at least part of the ends of the plurality of fiber filaments 142 are in contact with the liquid absorbing sheet 130, the other ends of the plurality of fiber filaments 142 are clamped between the atomizing base 160 and, the liquid absorbing sheet 130. Therefore, the position stability of wick 140 can be ensured, thus avoiding the wick 140 from disengaging from the liquid absorbing sheet 130 due to the gravity. Furthermore, at the end of the wick 140 where the plurality of fiber filaments 142 are separated, a length of the fiber filament 142 with ends being in contact with the liquid absorbing sheet 130 is less than a length of the fiber filament 142 with ends being clamped between the atomizing base 160 and the liquid absorbing sheet 130. The longer length of the fiber filament 142 which is clamped can ensure a sufficient contact area between the fiber filament 142 and the atomizing base 160 and the liquid absorbing sheet 130, thus increasing the clamping reliability. The shorter length of the fiber filament 142 which is in contact with the liquid absorbing sheet 130 can avoid the accumulation of the fiber filaments 142 at the position of the liquid absorbing sheet 130, which can lead to blocking of the liquid due to the squeezing of the fiber filaments 142. The shorter length of the fiber filament 142 which is in contact with the liquid absorbing sheet 130 can also facilitate the contact between the fiber filament 142 and the liquid absorbing sheet 130, thus further ensuring the liquid conducting rate of the fiber filament 142.

It should be noted that, FIG. 3 only shows an exemplary fiber filament 142 in a separated state, and the number of the fiber filament 142 can be more than three shown in FIG. 3. In addition, the fiber filaments 142 can be wound with each other.

Figure 7:
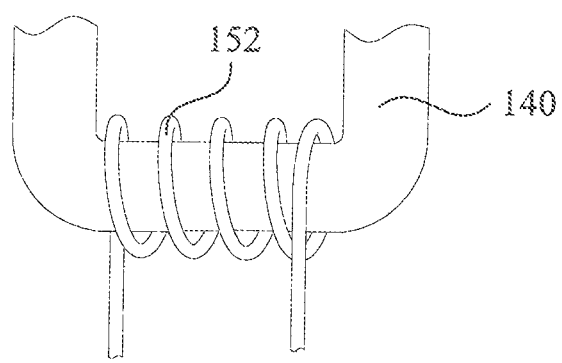
FIG. 7 illustrates a wick and an atomizing element of the atomizer for the inhaler of FIG. 1.

Referring to FIG. 7, the atomizing element includes a heating wire 152, which is coiled in a middle portion of the wick 140. Referring to FIG. 3, the first housing 112 defines an opening in communication with the air flow passage 113 and the atomizing cavity 161. The through hole 163 is in correspondence with the opening of the first housing 112. The heating wire 152 (now shown in FIG. 3) is positioned between the through hole 163 and the opening of the first housing 112. By setting the heating wire 152 at this place, the atomized liquid can be brought out by the air flow directly and not easily to be condensed on the inner wall of the atomizing cavity 161.

In one embodiment, a distance between the heating wire 152 and the first housing 112 is greater than 2 mm. The first housing 112 can be made of plastic, which tends to be deformed upon heating. The distance of more than 2 mm between the heating wire 152 and the first housing 112 can avoid the heating wire 152 from baking and deforming the first housing 112. In the test, the temperature of the heating wire 152 can be set to be 230° C., the first housing 112 is made of polycarbonate. The experimental data shows that, the first housing 112 will be baked to soft at the distance of 1.5 mm, 1.6 mm, 1.7 mm, 1.8 mm, and 1.9 mm, but will not be soften at the distance of 2.0 mm, 2.1 mm, 2.2 mm and 2.3 mm. The experiments further prove that the distance of more than 2 mm can avoid the heating wire 152 from baking and deforming the first housing 112.

Figure 8:
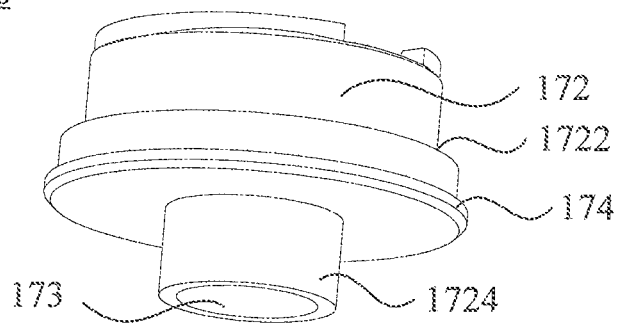
FIG. 8 is a perspective view of a negative electrode connecting element of the atomizer for the inhaler of FIG. 1.

Referring to FIG. 2, FIG. 3 and FIG. 8, in one embodiment, the atomizer 100 further includes a negative electrode connecting element 170. The negative electrode connecting element 170 includes a negative electrode connecting element body 172 and a boss 174. The boss 174 is located at an outer periphery of the negative electrode connecting element body 172 protruding, from the negative electrode connecting element body 172. The negative electrode connecting element body 172 and the boss 174 are both conductors. The negative electrode connecting element body 172 is electrically connected to the boss 174. The atomizing base 160 is received in the cavity 117 of the third housing 116. Part of the negative electrode connecting element body 172 extends inside the cavity 117 and is in contact with the atomizing base 160. The negative electrode connecting element body 172 is electrically connected to a negative electrode of the atomizing element. The negative electrode connecting element body 172 defines an air inlet 173 in communication with the air flow passage 113 and an outside of the negative electrode connecting element body 172.

The negative electrode connecting element 170 is a conductor, the negative electrode of the atomizing element is electrically connected to the negative electrode connecting element 170, the boss 174 of the negative electrode connecting element 170 can be used to be in contact with a sleeve of the inhaler, such that the atomizing element can be electrically connected to the sleeve via the negative electrode connecting element 170. When the atomizing element ages or the liquid in the atomizer 100 runs out, the user can replace the atomizer 100 only rather than replacing all components, thus reducing the cost and avoiding the waster. During the assembly and replacing of the atomizer 100, the user can insert the atomizer 100 into the sleeve from one end thereof until the boss 174 is in contact with an abutting portion of the sleeve, the operation is simple and convenient. After a power assembly is mounted, the power assembly can push the atomizer 100, thereby ensuring a circuit connecting reliability.

Furthermore, the boss 174 can have an annular shape. The boss 174 surrounds an outer periphery of the negative electrode connecting element body 172, thus increasing a connecting reliability of the boss 174 to the sleeve. In one embodiment, the negative electrode connecting element body 172 is provided with a stopped portion 1722 configured to be latched with the edge of the third housing 116.

Referring to FIG. 2, FIG. 3, and FIG. 8, in one embodiment, the negative electrode connecting element 170 further includes a connecting tube 1724 located at the air inlet 173. The connecting tube 1724 is connected to the negative electrode connecting element body 172. The connecting tube 1724 is a conductor and is electrically connected to the negative electrode connecting element body 172, such that the negative electrode connecting element body 172 is electrically connected to the negative electrode of the atomizing element via the connecting tube 1724.

Referring to FIG. 2 and FIG. 3, the atomizer 100 further includes a positive electrode connecting element 180 and an insulating sleeve 190. The positive electrode connecting element 180 is a conductor and is located at the air inlet 173. In the illustrated embodiment, the positive electrode connecting element 180 is at least partially received in the connecting tube 1724 to be electrically connected to the positive electrode of the atomizing element. The insulating sleeve 190 is sleeved on the positive electrode connecting element 180 and is located between the negative electrode connecting element 170 and the positive electrode connecting element 180, such that the negative electrode connecting element 170 is insulated from the positive electrode connecting element 180.

Figure 9:
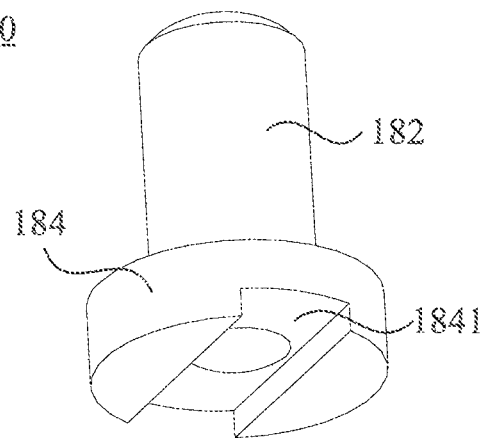
FIG. 9 is a perspective view of a positive electrode connecting element of the atomizer for the inhaler of FIG. 1.
Figure 10:
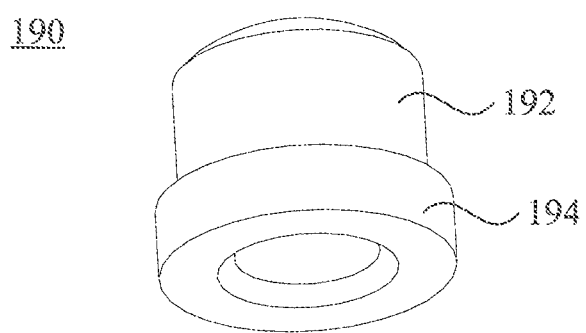
FIG. 10 is a perspective view of an insulating sleeve of the atomizer for the inhaler of FIG. 1.
Figure 11:
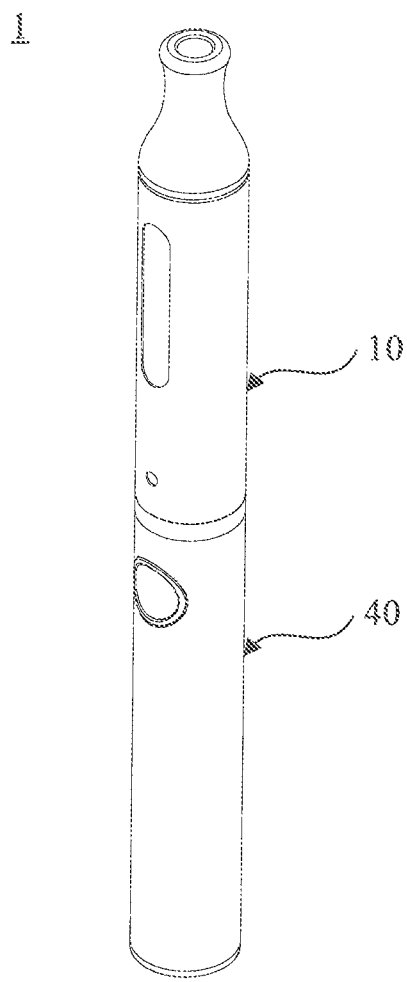
FIG. 11 is a perspective view of an embodiment of the inhaler.
Figure 12:
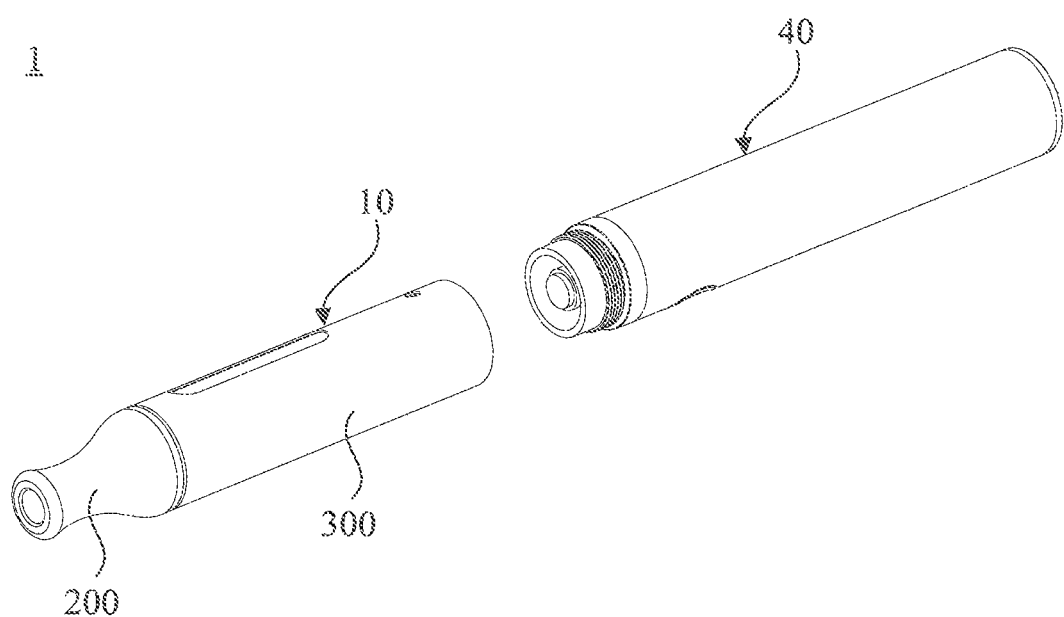
FIG. 12 is an exploded view of the inhaler of FIG. 11.
Figure 13:
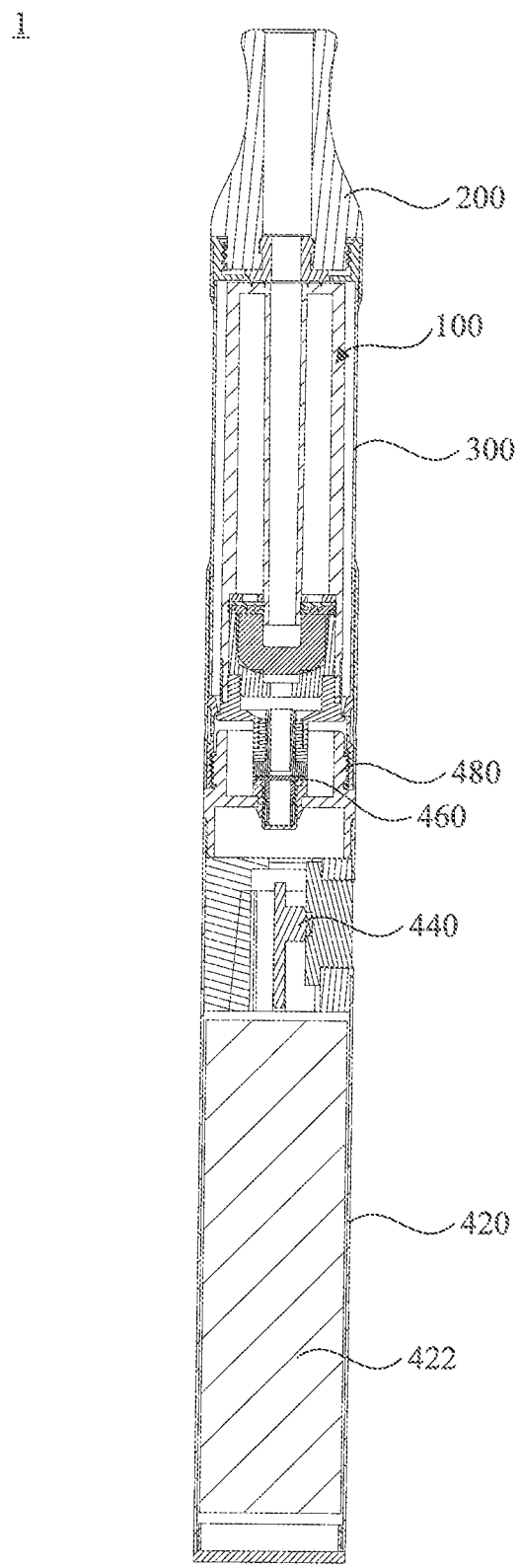
FIG. 13 is an cross-sectional view of the inhaler of FIG. 11.
Figure 14:
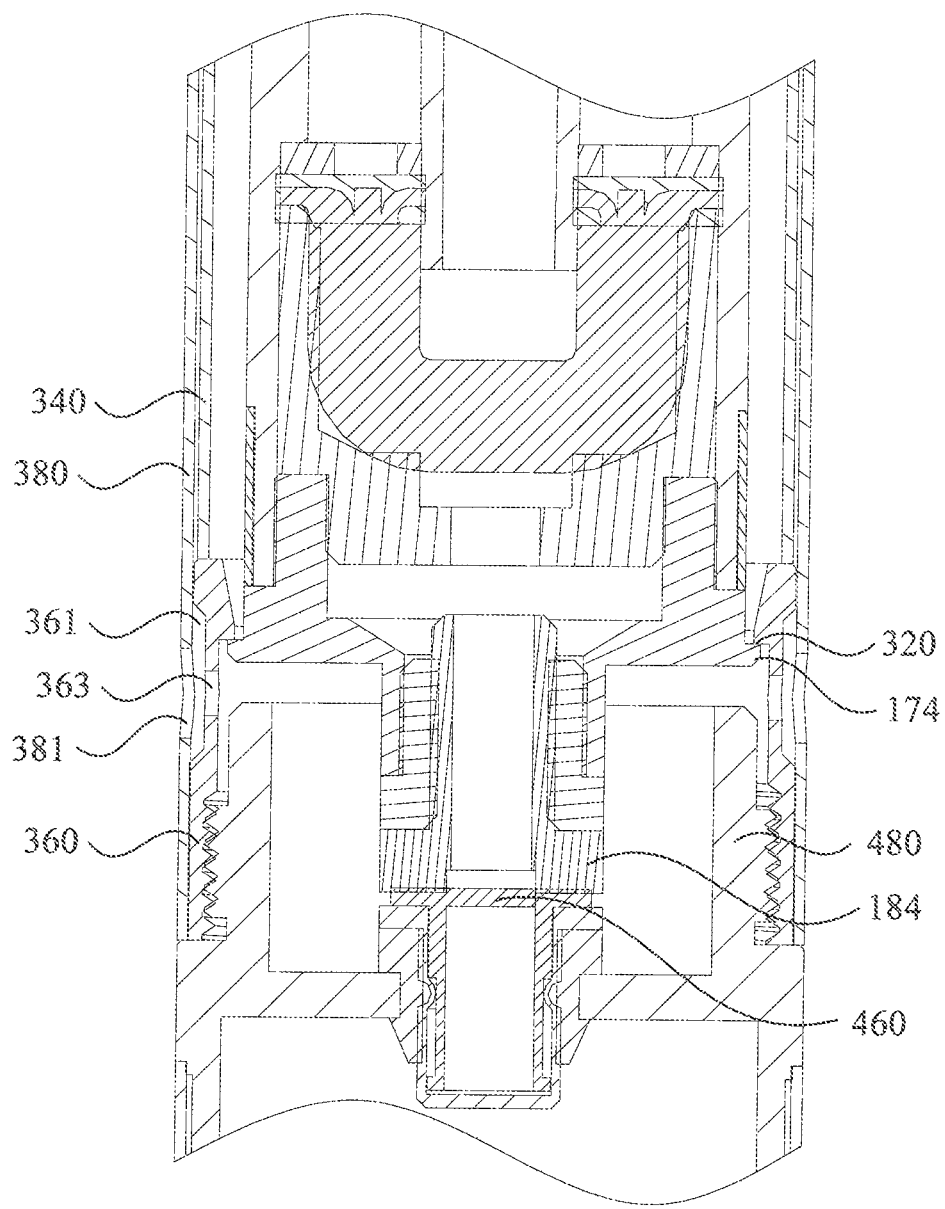
FIG. 14 is an partially enlarged view of the inhaler of FIG. 13.
Figure 15:
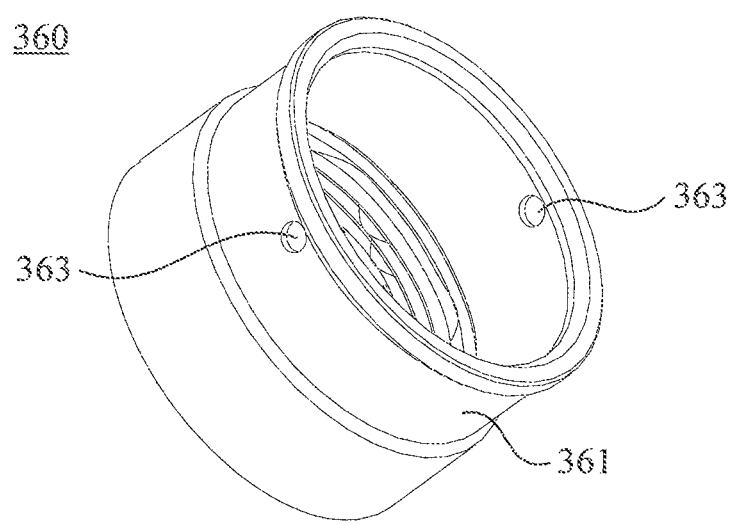
FIG. 15 is a perspective view of a second sleeve of the inhaler of FIG. 11.

Referring to FIG. 9, in one embodiment, the positive electrode connecting element 180 further includes a positive electrode connecting element body 182 and a latching portion 184. The positive electrode connecting element body 182 has a tubular shape and is at least partially received in the connecting tube 1724. The latching portion 184 is located at an end of the positive electrode connecting element body 182 protruding outwardly from a periphery of the positive electrode connecting element body 182. Referring to FIG. 10, the insulating sleeve 190 includes an insulating sleeve body 192 and a flange 194. The insulating sleeve body 192 has a tubular shape and is located between the positive electrode connecting element body 182 and the connecting tube 1724. The flange 194 is located at an end of the insulating sleeve body 192 protruding outwardly from a periphery of the insulating sleeve body 192. The flange 194 is located between the latching portion 184 and an end surface of the connecting tube 1724.

The latching portion 184 is configured to be in contact with the power assembly of the inhaler. The power assembly is usually threadedly connected to the sleeve. When the power assembly is screwed into the sleeve, an inner electrode thereof will be in contact with the latching portion 184. After the power assembly is fastened, the inner electrode will push the latching portion 184 inwardly, thus ensuring an electrical connecting reliability of the negative electrode connecting element 170 and the sleeve. Preferably, the latching portion 184 defines an air slot 1841 in communication with the inside of the positive electrode connecting element body 182 and the outside of the positive electrode connecting element 180. The positive electrode connecting element body 182 is tubular and has an inner passage in communication with the air flow passage 113. The air slot 1841 can prevent the air flow passage 113 from blocking, thus ensuring a smooth air flow in the inhaler.

Referring to FIG. 1 to FIG. 3, in one embodiment, the atomizer 100 is provided with a confining element 190a at an outside of the third housing 116. The confining element 190a has an annular shape and is located at a position where the third housing 116 is connected to the negative electrode connecting element body 172. The negative electrode connecting element body 172 partially extends into the cavity 117 and is connected to the third housing 116, and the confining element 190a can enhance their connection. The friction between the third housing 116 and the negative electrode connecting element body 172 can be enhanced by the confining element 190a, thus preventing them from disengaging. Furthermore, the third housing 116 defines a limiting groove 1161 at an end thereof. The confining element 190a is embedded in the limiting groove 1161 to increase the stability thereof.

Referring to FIG. 11 to FIG. 14, an embodiment of an inhaler 1 includes an atomizing assembly 10 and a power assembly 40. The power assembly 40 is fixed and electrically connected to the atomizing assembly 10. The inhaler 1 can be used to atomize the liquid into vapor, which then can be delivered into body. The inhaler 1 can be an electronic cigarette, or a medical metered-dose inhaler, or the like.

The atomizing assembly 10 includes a mouthpiece 200, a sleeve 300, and the described atomizer 100 shown in FIG. 1 to FIG. 10. The mouthpiece 200 is located at an end of the sleeve 300. The mouthpiece 200 and the sleeve 300 can be integrally formed or separated components. The atomizer 100 is located inside the sleeve 300 and can enter the sleeve 300 from the other end of the sleeve 300. In the illustrated embodiment, the sleeve 300 includes an abutting portion 320, which is a conductor. The abutting portion 320 can be in contact with the boss 174, thus implementing the electrical connection between the abutting portion 320 and the boss 174.

The sleeve 300 can include a first sleeve 340, a second sleeve 360, and a third sleeve 380, which are coaxially arranged. An end of the first sleeve 340 is in contact with an end of the second sleeve 360. The third sleeve 380 sleeves on the outside of the first sleeve 340 and the second sleeve 360, such that the first sleeve 340 and the second sleeve 360 are fixed together. The second sleeve 360 is a conductor, and the abutting portion 320 is located in an inner wall of the second sleeve 360, such that the abutting portion 320 is electrically connected to the second sleeve 360. The second sleeve 360 is provided with an internal thread, the power assembly 40 is provided with an external thread, such that the second sleeve is threadedly engaged with the power assembly 40. In alternative embodiments, the internal thread can be disposed on the power assembly 40, and the external thread can be disposed on the second sleeve 360.

Referring to FIG. 5, the second sleeve 360 further defines an annular groove 361 on an outer surface thereof. The second sleeve 360 defines a first vent 363 on the bottom of the groove 361. The third sleeve 380 defines a second vent 381 corresponding to the first vent 363. The configuration of the groove 361, the first vent 363, and the second vent 381 can ensure the communication between the air inlet 173 of the negative electrode connecting element body 172 and the outside of the inhaler 1. Preferably, the positions of the second vent 381 and the first vent 363 can be staggered, so as to avoid foreign matter from entering the inhaler 1.

In one embodiment, the power assembly 40 includes a main body 420, a power switch 440, a first connecting portion 460, and a second connecting portion 480. The main body 420 includes a battery 422. The second connecting portion 480 is provided with an external thread matching with the inner thread of the second sleeve 360 of the atomizing assembly 10, such that the second connecting portion 480 can be threadedly engaged with the atomizing assembly 10. The power assembly 40 can be easily assembled or disassembled from the atomizing assembly 10, such that when the battery 422 of the power assembly 40 is low, the power assembly 40 can be replaced or recharged, and when the liquid in the atomizing assembly 10 runs out, the atomizer 100 of the atomizing assembly 10 can be simply replaced.

The first connecting portion 460 can be located in the middle portion of the second connecting portion 480 and is electrically connected to a positive electrode of the battery 422. The first connecting portion 460 is insulated from the second connecting portion 480 by an insulating element or spacing them from a distance. After the second connecting portion 480 is threadedly engaged with the second sleeve 360, the first connecting portion 460 is in contact with and electrically connected to the latching portion 184 of the positive connecting element 180. Since the contact surface between the first connecting portion 460 and the latching portion 184 is relatively large, the electrical reliability of the positive electrode is increased. Meanwhile, the first connecting portion 460 can provide a pushing force to the latching portion 184 towards the inside of the sleeve 300, thus the electrical reliability between the negative electrode connecting element 170 and the sleeve 300 is increased. The power switch 440 is positioned on the main body 420. The user can simply turn on/off the power by switching a control circuit, thus it is convenient and saving energy.

In the inhaler 1, the liquid stored in the liquid reservoir 115 can reach the liquid, absorbing sheet 130 via the liquid conducting hole 122 on the gasket 120, such that it can be absorbed by the liquid absorbing sheet 130. The liquid of the liquid absorbing sheet 130 will then be absorbed by the wick 140, and finally atomized by the atomizing element. The gasket 120 has a very large liquid-passing rate, and the amount of liquid passing through the gasket 120 can be roughly controlled by the number and the diameter of the liquid conducting hole 122. The liquid absorbing sheet 130 has a low liquid-passing rate, and the amount of liquid passing through the liquid absorbing sheet 130 can be precisely controlled. Due to the cooperation of the gasket 120 and the liquid absorbing sheet 130, the control accuracy of the amount of the liquid of the wick 140 can be effectively increased.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. An atomizer for an inhaler, comprising:
a liquid reservoir for storing liquid;
a gasket configured to restrict flow of the liquid in the liquid reservoir, the gasket defining at least one liquid conducting hole having a non circular shape;
a liquid absorbing sheet configured to absorb the liquid in the liquid reservoir via the at least one liquid conducting hole;
a wick in contact with the liquid absorbing sheet and configured to draw the liquid from the liquid absorbing sheet; and
an atomizing element fixed to the wick and configured to atomize the liquid in the wick.

2. The atomizer according to claim 1, further comprising a first housing and a second housing, the first housing being at least partially positioned in the second housing, the first housing defining an air flow passage therein, the gasket being sleeved on the first housing, the liquid reservoir being formed between the first housing and the second housing.

3. The atomizer according to claim 2, further comprising a third housing formed by an edge of the second housing extending in a direction away from the second housing;
wherein the third housing defines a cavity therein, and the gasket and the liquid absorbing sheet are received in the cavity; the liquid absorbing sheet is in contact with an inner wall of the third housing on an edge thereof.

4. The atomizer according to claim 3, further comprising an atomizing base defining an atomizing cavity, wherein the atomizing base defines an opening at an end thereof and defines a through hole at the other end thereof in communication with the atomizing cavity and an outside; the wick is located in the atomizing cavity; an edge of the atomizing base having the opening is in contact with the liquid absorbing sheet.

5. The atomizer according to claim 4, wherein the atomizing base is made of elastic material and defines a wire through hole thereon; the atomizing element comprises a wire extending through the wire through hole.

6. The atomizer according to claim 4, wherein the wick comprises a plurality of fiber filaments; the plurality of fiber filaments located at the end of the wick are separated; at least part of the ends of the plurality of fiber filaments are in contact with the liquid absorbing sheet, the other ends of the plurality of fiber filaments are clamped between the atomizing base and the liquid absorbing sheet.

7. The atomizer according to claim 6, wherein at the end of the wick where the plurality of fiber filaments are separated, a length of the fiber filament with ends being in contact with the liquid absorbing sheet is less than a length of the fiber filament with ends being clamped between the atomizing base and the liquid absorbing sheet.

8. The atomizer according to claim 6, wherein the wick has two ends, each end of the wick is located on opposite sides of the first housing; the atomizing element comprises a heating wire coiled around a middle portion of the wick; the first housing defines an opening in communication with the air flow passage and the atomizing cavity; the through hole is in correspondence with the opening; the heating wire is positioned between the through hole and the opening, and a distance between the heating wire and the first housing is greater than 2 mm.

9. The atomizer according to claim 4, further comprising a negative electrode connecting element, wherein the negative electrode connecting element comprises a negative electrode connecting element body and a boss located at an outer periphery of the negative electrode connecting element body; the negative electrode connecting element body and the boss are conductors; the negative electrode connecting element body is electrically connected to the boss; the atomizing base is received, in the cavity of the third housing; part of the negative electrode connecting element body extends through the cavity and is in contact with the atomizing base; the negative electrode connecting element body is electrically connected to the atomizing element; the negative electrode connecting element body defines an air inlet in communication with the air flow passage and an outside of the negative electrode connecting element body.

10. An atomizing assembly for an inhaler, comprising:
a sleeve;
a mouthpiece located at an end of the sleeve; and
an atomizer received in the sleeve;
wherein the atomizer comprises:
a liquid reservoir for storing liquid;
a gasket configured to restrict flow of the liquid in the liquid reservoir, the gasket defining at least one liquid conducting hole having a non-circular shape;
a liquid absorbing sheet configured to absorb the liquid in the liquid reservoir via the at least one liquid conducting hole;
a wick in contact with the liquid absorbing sheet and configured to draw the liquid from the liquid absorbing sheet; and
an atomizing element fixed to the wick and configured to atomize the liquid in the wick.

11. An inhaler, comprising:
a power assembly;
an atomizing assembly fixed to the power assembly and electrically connected to the power assembly;
wherein the atomizing assembly comprises:
a sleeve;
a mouthpiece located at an end of the sleeve; and
an atomizer received in the sleeve;
wherein the atomizer comprises:
a liquid reservoir for storing liquid;
a gasket configured to restrict flow of the liquid in the liquid reservoir, the gasket defining at least one liquid conducting hole having a non-circular shape;
a liquid absorbing sheet configured to absorb the liquid in the liquid reservoir via the at least one liquid conducting hole;
a wick in contact with the liquid absorbing sheet and configured to draw the liquid from the liquid absorbing sheet; and
an atomizing element fixed to the wick and configured to atomize the liquid in the wick.

\* \* \* \* \*